United States Patent
Pfister et al.

(10) Patent No.: US 7,761,135 B2
(45) Date of Patent: Jul. 20, 2010

(54) METHOD AND DEVICE FOR CORRECTION MOTION IN IMAGING DURING A MEDICAL INTERVENTION

(75) Inventors: Marcus Pfister, Bubenreuth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 763 days.

(21) Appl. No.: 11/636,953

(22) Filed: Dec. 11, 2006

(65) Prior Publication Data

US 2007/0167721 A1 Jul. 19, 2007

(30) Foreign Application Priority Data

Dec. 14, 2005 (DE) ........................ 10 2005 059 804

(51) Int. Cl.
*A61B 5/05* (2006.01)
(52) U.S. Cl. ................. 600/424; 600/407; 600/425; 600/426; 600/427; 382/128; 382/130; 382/131; 382/132
(58) Field of Classification Search ................. 600/407, 600/424, 425, 427; 382/128, 130, 131, 132
See application file for complete search history.

(56) References Cited

U.S. PATENT DOCUMENTS

| | | | | |
|---|---|---|---|---|
| 6,614,871 | B1 * | 9/2003 | Kobiki et al. ................. | 378/20 |
| 6,628,977 | B2 | 9/2003 | Graumann et al. | |
| 6,837,892 | B2 * | 1/2005 | Shoham ....................... | 606/130 |
| 7,327,872 | B2 * | 2/2008 | Vaillant et al. ............... | 382/154 |
| 7,505,809 | B2 * | 3/2009 | Strommer et al. ............ | 600/424 |
| 7,567,834 | B2 * | 7/2009 | Clayton et al. ............... | 600/424 |
| 2004/0215071 | A1 * | 10/2004 | Frank et al. .................. | 600/407 |
| 2005/0027193 | A1 | 2/2005 | Mitschke et al. | |
| 2006/0078195 | A1 | 4/2006 | Vaillant et al. | |
| 2007/0172024 | A1 * | 7/2007 | Morton et al. ................ | 378/10 |

FOREIGN PATENT DOCUMENTS

| | | |
|---|---|---|
| DE | 199 63 440 A1 | 7/2001 |
| DE | 103 23 008 A1 | 12/2004 |
| DE | 10 2005 050 000 A1 | 4/2006 |

OTHER PUBLICATIONS

Lothar Baetz, et al, "Imaging Systems for Medical Diagnostics", Fundamentals, Technical Solutions and Applications for Systems Applying Ionizing Radiation, Nuclear Magnetic Resonance and Ultrasound, Nov. 2005, pp. 2-5, 62-83, ISBN 3-89578-226-2, Publicis Corporate Publishing, Erlangen Germany.

* cited by examiner

*Primary Examiner*—Brian Casler
*Assistant Examiner*—Baisakhi Roy

(57) ABSTRACT

The present invention relates to a method and a device for correcting motion in imaging during a medical intervention, by which method a 3D tomographic image of a target area for the intervention is first recorded while there are one or more medical instruments in the target area that will remain there during the intervention. During the intervention 2D fluoroscopic images of the target area are recorded and registered with the 3D image. The registration is therein adjusted for each 2D fluoroscopic image in realtime based in each case on the one or more instruments. The 2D fluoroscopic images are then in each case visualized with representations, concurring in terms of perspective, of the 3D image. Virtually error-free overlaying of the 3D image with in each case one 2D fluoroscopic image can be implemented using the present method and associated device.

13 Claims, 3 Drawing Sheets

METHOD AND DEVICE FOR CORRECTION MOTION IN IMAGING DURING A MEDICAL INTERVENTION

CROSS REFERENCE TO RELATED APPLICATIONS

This application claims priority of German application No. 10 2005 059 804.8 filed Dec. 14, 2005, which is incorporated by reference herein in its entirety.

FIELD OF THE INVENTION

The present invention relates to a method and a device for correcting motion in imaging during a medical intervention.

BACKGROUND OF THE INVENTION

During a medical intervention, realtime images that serve to navigate the instruments being used and on which the inserted medical instrument is discernible are obtained and presented with the aid of fluoroscopy. Although not showing any spatial three-dimensional details, said 2D fluoroscopic images are nonetheless quickly available and will minimize the patient's and physician's exposure to radiation. For improving navigation it is known to register preoperatively recorded 3D images with the 2D fluoroscopic images and underlay these in a suitable representation. The spatial information missing from the 2D fluoroscopic images is conveyed in this way. Combining registered 2D and 3D images will then improve the physician's orientation within the targeted volume.

The 3D image can be registered with the 2D fluoroscopic images employing different techniques that utilize natural landmarks or artificial landmarks applied to the body, or correlations specific to the equipment used. During said 2D/3D image registration it is determined from which direction the 3D volume encompassed by the 3D image has to be projected so it can be made to coincide with the 2D image. A problem with 2D/3D registration, particularly in the case of abdominal applications such as, for instance, liver biopsies, is that the preoperatively recorded 3D image is static, whereas respiratory movements are clearly discernible in the 2D fluoroscopic images. That leads to errors in the overlaid representation with the projected 3D image.

SUMMARY OF THE INVENTION

The object of the present invention is hence to disclose a method and a device for correcting motion in imaging during a medical intervention with both of whose aid errors of said type are avoided in the overlaid representation of the 2D fluoroscopic images by means of a suitable representation of the 3D image.

Said object is achieved using the method and device according to the independent claims. Advantageous embodiments of the method and device are the subject of the dependent claims or can be derived from the following description and from the exemplary embodiments.

In the case of the method proposed for correcting motion in imaging during a medical intervention a 3D tomographic image of a target area for the intervention is, in a known manner, recorded in advance and registered with fluoroscopic 2D images of the target area that are recorded sequentially during the intervention, with one or more representations concurring in terms of perspective with the 2D fluoroscopic images being computed from the 3D image and visualized jointly with the 2D fluoroscopic images. The present method is characterized in that the 3D image of the target area is recorded while there are one or more medical instruments in the target area that will also remain there during the intervention. Said one or more medical instruments are identified both in the 3D image and in the 2D fluoroscopic images. That can be done by applying, for example, known segmenting techniques. The registration with the 3D image is performed or adjusted for each 2D fluoroscopic image in realtime based on the one or more identified instruments.

In the case of the present method and associated device the 2D/3D registration is therefore performed again or adjusted for each 2D fluoroscopic image using the instruments identified in the images so that any motion in the target area for the intervention will be compensated in the joint representation of the images. Said motion can be, for example, respiratory movements, organ movements, or the patient's own movements. A major feature of the present method and associated device is that a medical instrument is used for the registration or, as the case may be, adjusting the registration that is introduced into the target area before the 3D image is recorded, and remains there during the intervention. Said instrument can be one that is used for the intervention, for example a catheter or puncture needle. An additional instrument can, though, also be employed that will not otherwise be further used during the intervention. Said instrument can also be, for example, a puncture needle or catheter.

In the case of the present method the 2D/3D registration can take place based solely on the instrument identified in the images, with the possibility, of course, of there also being a plurality of instruments. It is, though, also possible first to perform a 2D/3D registration with the first 2D fluoroscopic image based on other information or with the additional inclusion of other information. Examples of suitable registration techniques can be found in, for example, A. Oppelt (editor): Imaging Systems for Medical Diagnostics, pages 65 to 82, published by Publicis Verlag, November 2005. Said registration is then adjusted in the subsequent 2D fluoroscopic images on the basis of the instruments identified in the images, with the instrument identified in the 3D image being in all cases imaged onto the instrument identified in the 2D fluoroscopic image in such a way that the two instruments will coincide. The imaging or, as the case may be, transformation required therefor corresponds to the registration, which is hence performed again or, as the case may be, adjusted for each new 2D fluoroscopic image.

It is not necessary to subject the entire identified instrument to the above-cited imaging. Rather it will in many cases suffice to use a section of said instrument for the registration. That will be necessary particularly when a catheter that is moved along a hollow canal during the intervention is employed as the medical instrument. In this case the section of the instrument positioned at a salient location within the hollow canal, for example a characteristic bend, can then be used each time for the purpose of registration.

A development of the present method and associated device employs a medical instrument having special markings discernible in both the 3D image and the 2D fluoroscopic images. Said markings can be, for example, a geometric structure or material areas on the instrument that are differently permeable to x-radiation. The 2D/3D registration is made easier by the markings. Thus, for example, the angle at which a puncture needle or catheter is positioned relative to the focal plane of the 2D fluoroscopic image can be registered directly using two markings spaced apart along the needle's or catheter's longitudinal axis.

The 3D tomographic image can be recorded using different tomographic imaging techniques, for example by means of computer-assisted tomography or magnetic resonance imaging. The 3D angiography technique is particularly advantageous because a C-arm x-ray device can be employed therefor that subsequently will also serve to produce the 2D fluoroscopic recordings. In that case the intervention can take place immediately after the 3D image has been recorded and without moving the patient elsewhere. The 2D/3D registration will also be simplified as a result of the images' being recorded using the same system.

The registered images can be visualized, which is to say in each case one 2D fluoroscopic image can be displayed jointly with a representation of the 3D image concurring in terms of perspective with the 2D fluoroscopic image, in a known manner according to the prior art. The two images are generally overlaid one over the other employing a suitable technique, with its likewise being possible for the 3D image to be represented in different ways, for example in MIP (Maximum Intensity Projection) or MPR (Multi-Planar Reformatting) form.

The present device, embodied for implementing the method, includes an input interface for image data of a 3D tomographic image and for image data of 2D fluoroscopic images, a first identification module enabling one or more medical instruments to be identified in the 3D image automatically or interactively, a second identification module identifying said one or more medical instruments in the 2D fluoroscopic images automatically, a registration module for 2D/3D registration between the 3D image and 2D fluoroscopic images, and a visualization module which from the 3D image computes one or more representations concurring in terms of perspective with the 2D fluoroscopic images and visualizes it/them jointly with the 2D fluoroscopic images. The registration module is therein embodied such as to register each 2D fluoroscopic image with the 3D image, or adjust such registering, in realtime based on the one or more identified instruments.

The present method and associated device are suitable for imaging during any interventions during which motion in the target area has to be corrected. Besides movements due to respiration, this relates also to other organ movements, for example heartbeats during cardiological or electro-physiological interventions, or the patient's own movements. The method described and the associated device offer particular advantages especially in connection with abdominal applications such as, for example, liver biopsies. Movements of the liver being relatively decoupled from the surface of the skin, motion cannot here be corrected based on artificial landmarks secured to the skin's surface. On the other hand, several punctures are often necessary for a liver biopsy in order to reach the desired target location. Inserting a puncture needle before the 3D image recording is made enables the physician to be provided with error-free image information for the remainder of the intervention so that targeting accuracy for the biopsy itself will be improved.

BRIEF DESCRIPTION OF THE DRAWINGS

The present method and associated device are briefly explained again below with reference to exemplary embodiments and in conjunction with the drawings, without limiting the scope of protection set by the claims.

DETAILED DESCRIPTION OF THE INVENTION

The method is explained in the first example that follows with the aid of a liver intervention during which a catheter is navigated into the liver. Both in this example and in that which follows, the patient is positioned on a C-arm device by means of which both the 3D image and the 2D fluoroscopic images are recorded.

Figure 4:
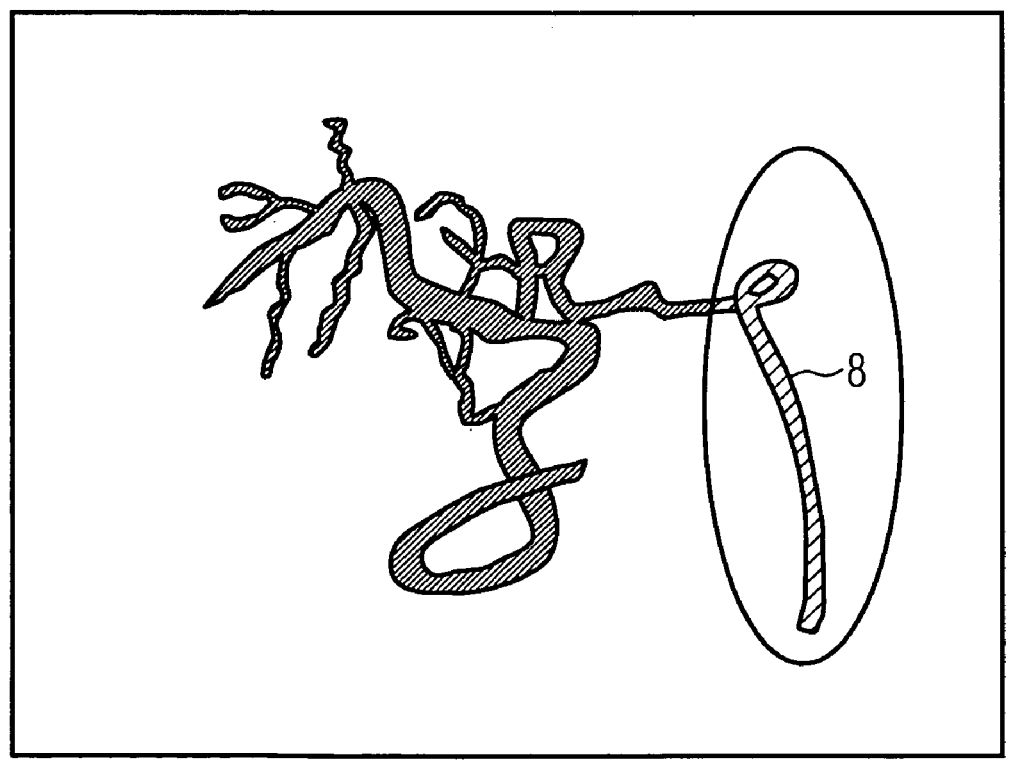
FIG. 4 is an example of a 3D angiographic image with a catheter having been inserted.

The physician first navigates the catheter into the liver. Using the C-arm device, the physician then records a 3D angiographic image of the liver containing the catheter. FIG. 4 is an example of a 3D angiographic image of said type in which the catheter 8 is discernible. The catheter 8 is marked in said reconstructed 3D image by the physician or segmented automatically to distinguish it from other structures.

Figure 3:
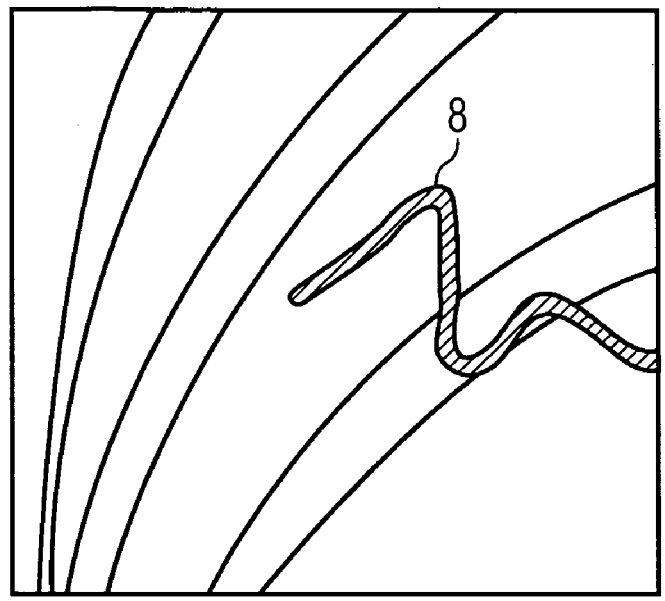
FIG. 3 is an example of a 2D fluoroscopic image with a catheter having been inserted.

The physician then performs the intervention while 2D fluoroscopic recordings are being made using the C-arm device. The first 2D fluoroscopic image is therein first registered using the known system parameters from which the geometry data or, as the case may be, projection data needed for the registration can be derived. The device is calibrated beforehand for this purpose. The catheter 8 is discernible in the respective 2D fluoroscopic images, as can be seen by way of example from FIG. 3 showing a fluoroscopic image of said type. The catheter is segmented in the fluoroscopic image by means of a suitable image processing method based on, for example, a threshold technique, and made to coincide with the catheter marked in the 3D volume of the 3D image. That is done in realtime.

Due to the movement of the liver during the intervention, various transformations, as a rule translations and rotations, are computed in order to achieve coincident imaging. The original registration is then updated in realtime using the respective said transformations so that the 2D fluoroscopic image is represented overlaid with the corresponding projection of the 3D image in each case virtually error-free.

Figure 1:
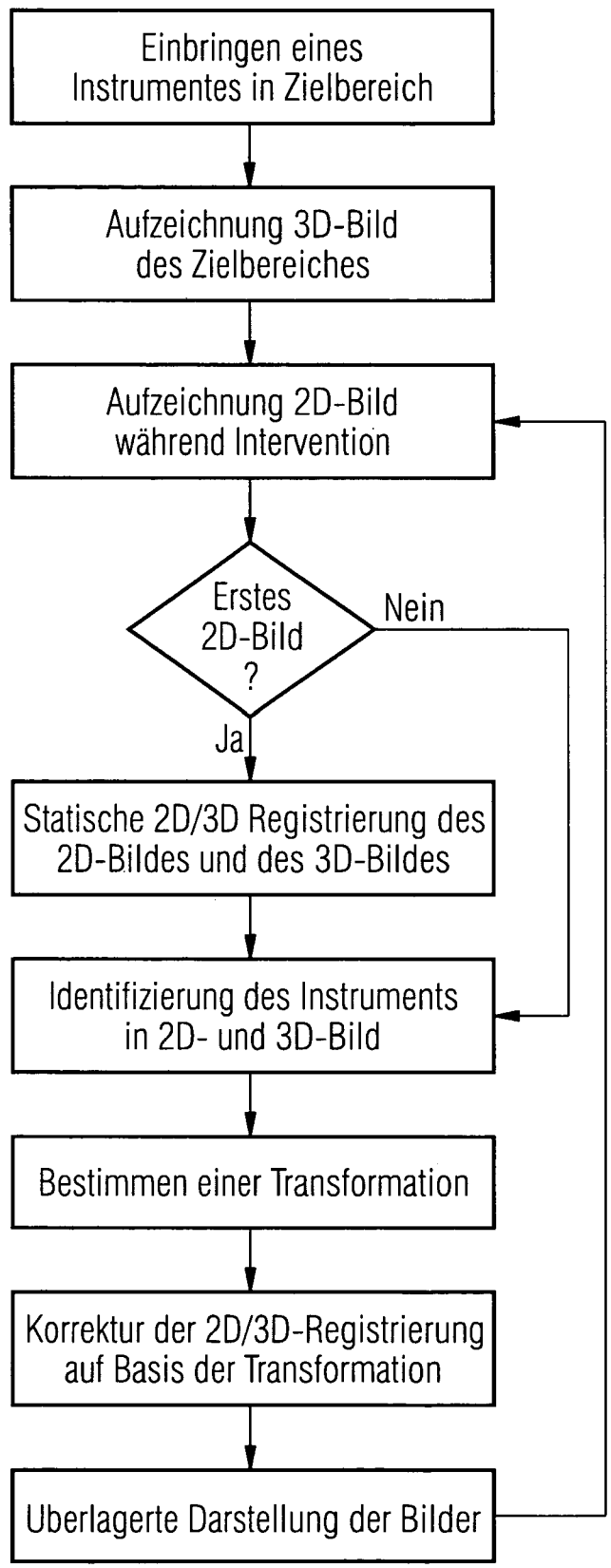
FIG. 1 is a schematic of the procedural flow of the present method.

This process is illustrated schematically in FIG. 1.

Instead of using the catheter employed for the intervention, a further catheter, having special markings, can be inserted exclusively for the purpose of respiration-compensated registration while the intervention is being performed using the other catheter. Another instrument can, of course, also be used, as will be explained below using a liver biopsy as an exemplary instance.

In the case of said liver biopsy the physician inserts a specially marked needle into the liver before the 3D image is recorded. The physician then records a 3D angiographic image of the liver, which image includes said needle. The needle is marked in the reconstructed 3D image or automatically segmented to distinguish it from other structures. The physician then punctures the liver with a second needle. In the first fluoroscopic image registered statically with respect to the reconstructed 3D volume of the 3D image the marking needle is segmented by means of a suitable image processing method and, by means of a suitable method, made to coincide with the marking needle located in the 3D volume. This transformation takes place in realtime. The registration is then updated in realtime on the basis of the computed displacement and/or rotation (transformation) so that the representation of the overlaid image can also take place here virtually without delay and free of errors.

Figure 2:
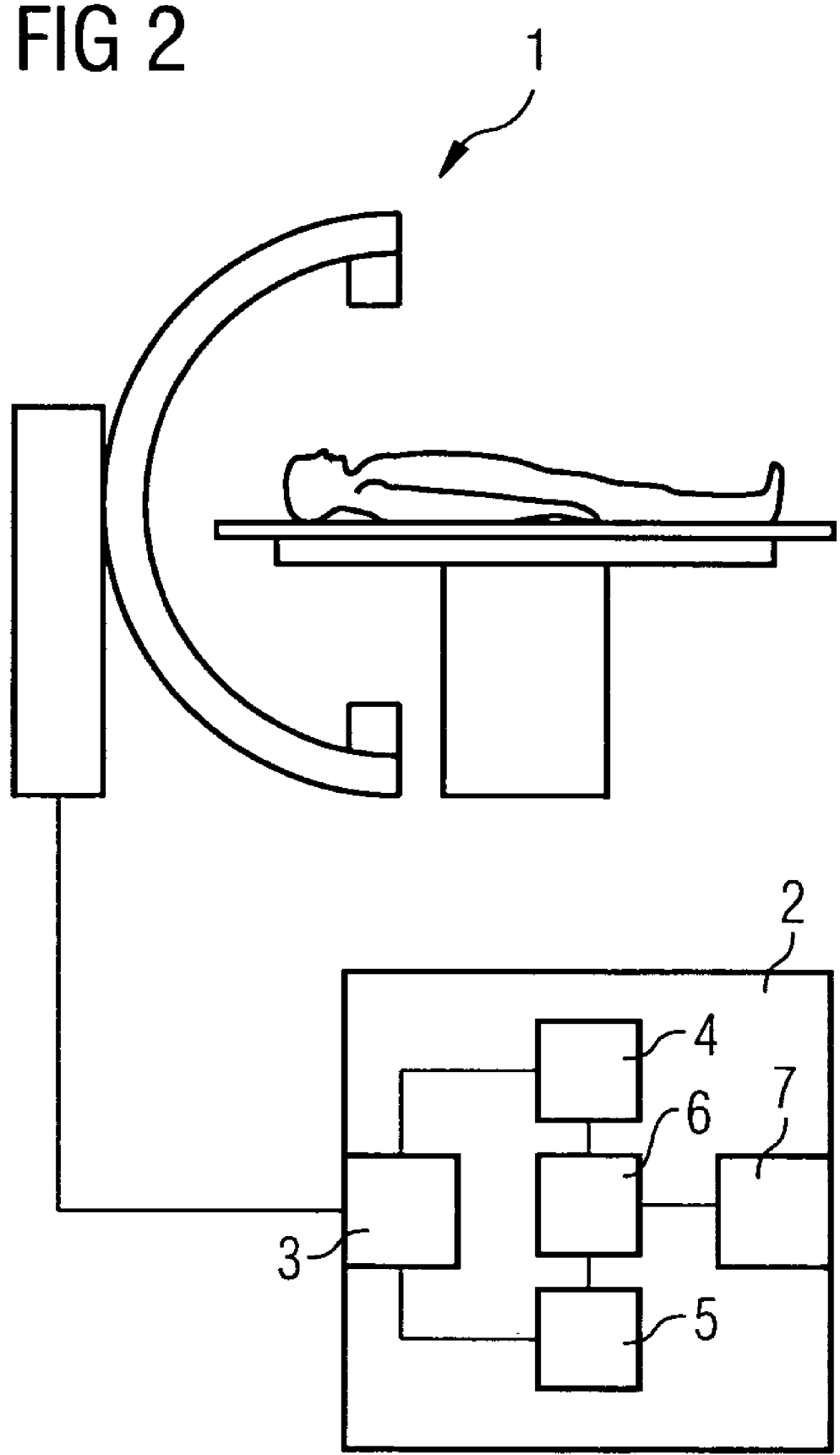
FIG. 2 is a schematic of the physical structure of the present device.

The device employed for the two exemplary applications is again shown schematically in FIG. 2. Said device consists in this example of a C-arm x-ray system 1 connected to a data processing system 2. The image data of the 3D image and of the 2D fluoroscopic images is obtained from the C-arm system 1 via the input interfaces 3 of the data processing system 2. The medical instrument discernible in the images is identified, in particular segmented, in the two identification modules 4, 5. A registration module 6 registers the 2D fluoroscopic images with the 3D image or adjusts an already performed registration based on the identified instruments. Based on said registration, the respectively current 2D fluoroscopic image is then overlaid with a suitable projection of the 3D image and displayed on a monitor, not shown in the figure, by the visualization module 7.

The invention claimed is:

1. A method for correcting a motion in an imaging during a medical intervention on a patient, comprising:
    inserting a medical instrument into a target area of the patient;
    recording a 3D tomographic image of the target area of the patient comprising the instrument;
    recording a 2D fluoroscopic image of the target area during the intervention;
    identifying at least a section of the medical instrument in both the 2D fluoroscopic image and the 3D tomographic image;
    registering the 2D fluoroscopic image with the 3D tomographic image using said identified section of the medical instrument in the 2D fluoroscopic image and the 3D tomographic image;
    computing a representation from the 3D tomographic image respectively concurring with the 2D fluoroscopic image based on the registering;
    due to a movement of the target area in a real time, adjusting in said real time deviations in the concurrent image representation by registering the 2D fluoroscopic image with the computed representation of the 3D tomographic image using said identified section of the medical instrument; and
    upon performing said adjusting, jointly displaying the 2D fluoroscopic image and the representation of the 3D tomographic image.

2. The method as claimed in claim 1, wherein a further 2D fluoroscopic image is recorded sequentially during the intervention and the steps of identifying, computing, adjusting, and displaying are repeated based on the further recorded 2D fluoroscopic image.

3. The method as claimed in claim 1, wherein the 3D tomographic image and the 2D fluoroscopic image are recorded using a C-arm x-ray device.

4. The method as claimed in claim 1, wherein the 3D tomographic image is recorded using a 3D angiography method.

5. The method as claimed in claim 1, wherein the medical instrument in the 2D fluoroscopic image is identified using an automatic image processing method.

6. The method as claimed in claim 1, wherein the 2D fluoroscopic image and the representation of the 3D image are displayed by overlaying one over the other.

7. The method as claimed in claim 1, wherein the medical instrument comprises a special marking that is discernible in the 3D tomographic image and the 2D fluoroscopic image.

8. The method as claimed in claim 1, wherein the medical instrument is a puncture needle.

9. The method as claimed in claim 1, wherein the medical instrument is a catheter.

10. A device for correcting a motion in an imaging during a medical intervention on a patient, comprising:
    a C-arm x-ray device that generates a 3D tomographic image of a target area of the patient and a 2D fluoroscopic image of the target area during the medical intervention;
    an input interface that inputs the 3D tomographic image and the 2D fluoroscopic image;
    a first identification device that identifies at least a section of a medical instrument for performing the intervention in the 3D tomographic image;
    a second identification device that automatically identifies said section of the medical instrument in the 2D fluoroscopic image;
    a computing device that:
        registers the 2D fluoroscopic image with the 3D tomographic image based on said identified section of the medical instrument in the 2D fluoroscopic image and the 3D tomographic image,
        computes a representation from the 3D tomographic image respectively concurring with the 2D fluoroscopic image, and
        due to a movement of the target area in a real time, adjusts in said real time deviations in the concurrent image representation by registering the 2D fluoroscopic image with the computed representation using said identified section of the medical instrument; and
    a display device that displays the representation jointly with the 2D fluoroscopic image.

11. The device as claimed in claim 10, wherein the display device displays the representation of the 3D tomographic image and the 2D fluoroscopic image by overlaying one over the other.

12. The device as claimed in claim 10, wherein a further 2D fluoroscopic image is recorded sequentially during the intervention.

13. The device as claimed in claim 12, wherein a further representation from the 3D tomographic image perspectively concurring with the further 2D fluoroscopic image is computed and the registration is adjusted by registering the further 2D fluoroscopic image with the further computed representation in a real time.

* * * * *